(12) United States Patent
Ozawa et al.

(10) Patent No.: US 11,243,094 B2
(45) Date of Patent: Feb. 8, 2022

(54) DETECTING METHOD, DETECTING DEVICE, AND DETECTING SYSTEM

(71) Applicant: PANASONIC INTELLECTUAL PROPERTY CORPORATION OF AMERICA, Torrance, CA (US)

(72) Inventors: Jun Ozawa, Ibaraki (JP); Takahiro Hiyama, Osaka (JP); Yoshikuni Sato, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 259 days.

(21) Appl. No.: 16/413,898

(22) Filed: May 16, 2019

(65) Prior Publication Data

US 2019/0353501 A1    Nov. 21, 2019

(30) Foreign Application Priority Data

May 17, 2018    (JP) .............................. JP2018-095593

(51) Int. Cl.
| | | |
|---|---|---|
| *A61B 5/11* | (2006.01) | |
| *G01C 22/02* | (2006.01) | |
| *G01P 15/18* | (2013.01) | |

(52) U.S. Cl.
CPC ............ *G01C 22/02* (2013.01); *A61B 5/1118* (2013.01); *A61B 5/1123* (2013.01); *G01P 15/18* (2013.01)

(58) Field of Classification Search
CPC ....... G01C 22/02; G01P 15/18; A61B 5/1123; A61B 5/1118; A61B 5/486; A61B 5/112; A61B 5/1038; A61B 5/6807; A61B 2562/0219; A61B 2562/0247
See application file for complete search history.

(56) References Cited

U.S. PATENT DOCUMENTS

| | | | |
|---|---|---|---|
| 10,182,746 B1* | 1/2019 | Demiralp | ............. A61B 5/1123 |
| 2012/0209149 A1 | 8/2012 | Yoneyama et al. | |
| 2014/0276242 A1* | 9/2014 | Chen | ..................... A61B 5/1116 600/595 |

(Continued)

FOREIGN PATENT DOCUMENTS

| | | |
|---|---|---|
| JP | 2006-284404 | 10/2006 |
| JP | 2010-005033 | 1/2010 |

(Continued)

*Primary Examiner* — Eyob Hagos
(74) *Attorney, Agent, or Firm* — Greenblum & Bernstein, P.L.C.

(57) ABSTRACT

A detecting device obtains a first body motion signal from a body motion sensor while a person walks with a predetermined stride, the body motion sensor being attached to a body of the person and configured to detect a body motion of the person, obtains a reference-walk-waveform from a memory, the reference-walk-waveform being generated from a second body motion signal obtained from the body motion sensor while the person walks with the predetermined stride with the body motion sensor attached to an initially attached position, compares the obtained reference-walk-waveform with a waveform of the obtained first body motion signal to determine whether an attached position of the body motion sensor is shifted from the initially attached position, and outputs a determination result.

9 Claims, 7 Drawing Sheets

(56) References Cited

U.S. PATENT DOCUMENTS

| | | | |
|---|---|---|---|
| 2014/0309962 A1* | 10/2014 | Bauchot | A61B 5/6807 |
| | | | 702/150 |
| 2016/0166880 A1 | 6/2016 | Nakajima | |
| 2016/0262685 A1* | 9/2016 | Wagner | A61B 5/1123 |
| 2016/0372990 A1* | 12/2016 | Williamson | H02K 7/1853 |
| 2018/0264320 A1* | 9/2018 | Chang | A61B 5/1122 |
| 2019/0150793 A1* | 5/2019 | Barth | A61B 5/7267 |

FOREIGN PATENT DOCUMENTS

| | | |
|---|---|---|
| JP | 2010-259469 | 11/2010 |
| JP | 2011-251167 | 12/2011 |
| JP | 2013-244055 | 12/2013 |
| JP | 2016-112108 | 6/2016 |

* cited by examiner

FIG.1

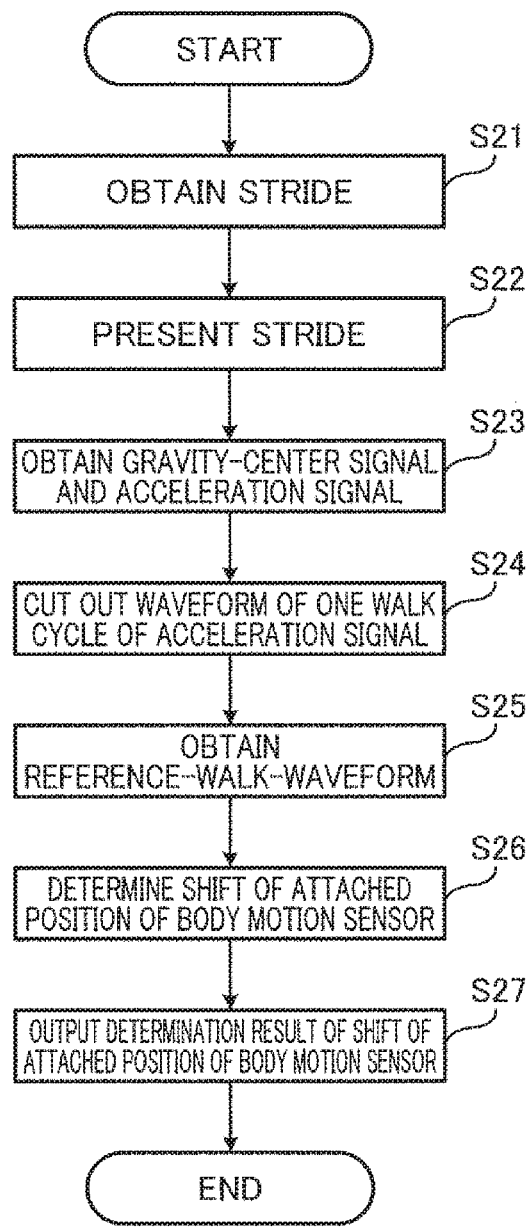

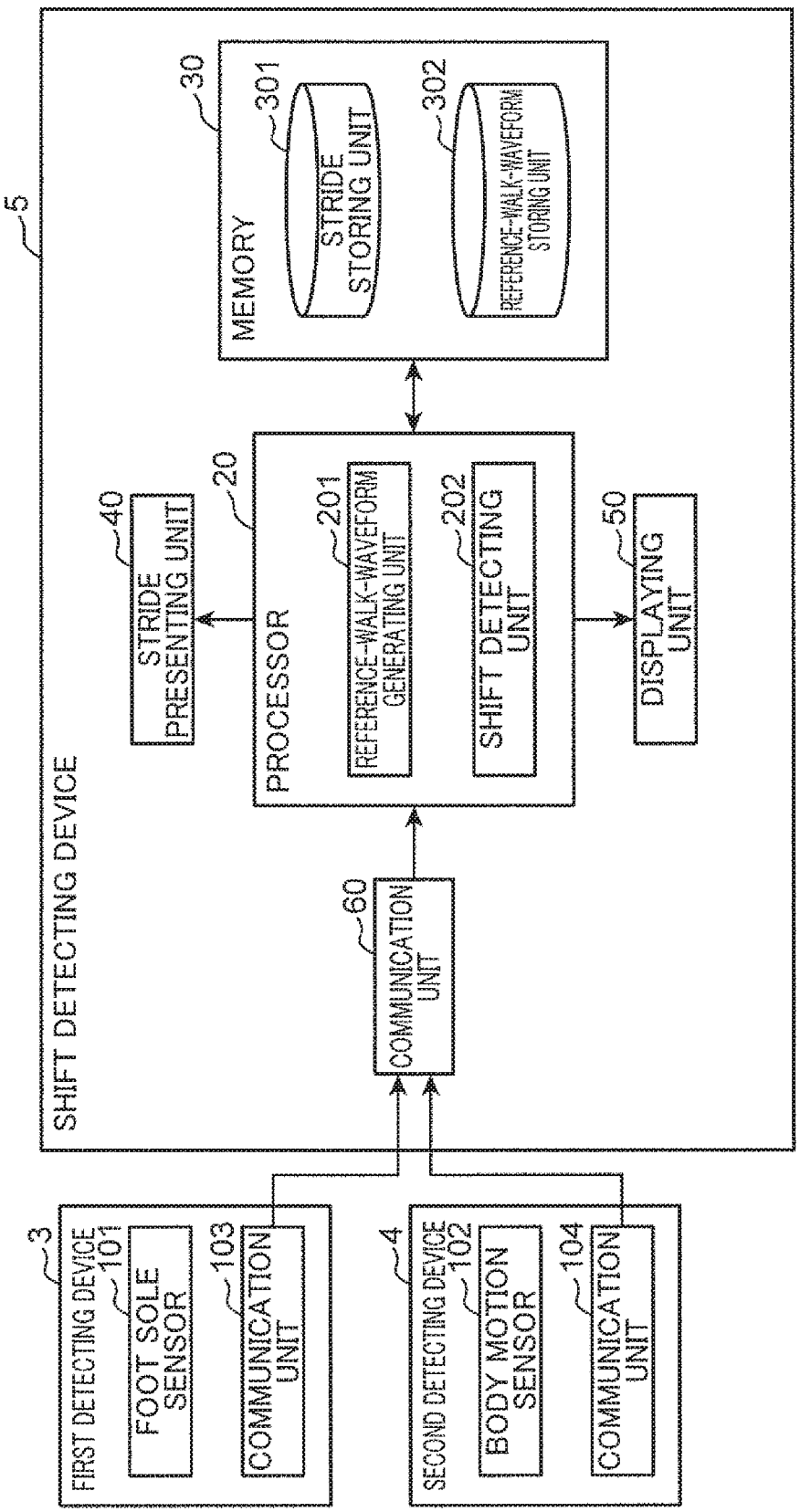

DETECTING METHOD, DETECTING DEVICE, AND DETECTING SYSTEM

FIELD OF THE INVENTION

The present disclosure relates to a detecting method, a detecting device, and a detecting system that detect a shift of a sensor, attached to a human body, from an initially attached position.

BACKGROUND ART

In recent years in the aging society, nursing care for elderly people has been focused. In particular, estimating a motor function of an elderly person prevents happening of an unpredictable accident, such as falling down, due to weakened muscles. Furthermore, a level to which the motor function has recovered by nursing care or rehabilitation can be gauged by estimating the motor function. Thus, information on the estimated motor function can be very useful for a nursing care worker and medical personnel. The physical condition of a person, not only of an elderly person, can be gauged by checking the motor function, and thus, the estimation of a motor function may become a technique of great demand.

In many cases, a sensor attached to a wrist, an ankle, or a waist is used to estimate a motor function of a person. To estimate the motor function or the health condition correctly, the sensor is calibrated after attached to the human body, namely, calibrated at an initially attached position. In a case where the sensor is attached by a belt or the like, the belt might become loose by a motion of a user, and the sensor might shift from the initially attached position.

In view of such a shift of the sensor, for example, JP 2010-259469 A discloses a wearable measuring device calculates the position of the foot of a second leg relative to the position of the foot of a first leg using a camera fixed to the wearable measuring device attached to the first leg of a user, stores the initially fixed position of the camera relative to the first leg, calculates the position of the camera relative to the first leg from an image of the first leg captured by the camera, calculates the positional shift amount between the stored initially fixed position and the calculated relative position, and corrects the calculated relative position of the foot of the second leg using the positional shift amount.

For example, JP 2013-244055 A discloses an information processing device that evaluates the balance from a body motion signal, estimates the moving direction of a living body, and detects from the estimated moving direction a shift of the attached position of a body motion signal detecting device.

However, in the prior art described above, the positional shift of the sensor cannot be detected accurately from a walking motion in some situations, so that further improvement is yet needed.

SUMMARY OF THE INVENTION

The present disclosure is made in view of solving the problem described above. An object of the present disclosure is to provide a detecting method, a detecting device, and a detecting system that detect a positional shift of an attached position, of a body motion sensor, from an initially attached position with high accuracy from a walking motion of a person.

A detecting method according to one embodiment of the present disclosure is performed by a computer, and the computer obtains a first body motion signal from a body motion sensor while a person walks with a predetermined stride, the body motion sensor being attached to a body of the person and configured to detect a body motion of the person, obtains a reference-walk-waveform from a memory, the reference-walk-waveform being generated from a second body motion signal obtained from the body motion sensor while the person walks with the predetermined stride with the body motion sensor attached to an initially attached position, compares the obtained reference-walk-waveform with a waveform of the obtained first body motion signal to determine whether an attached position of the body motion sensor is shifted from the initially attached position, and outputs a determination result.

BRIEF DESCRIPTION OF THE DRAWINGS

FIG. 1 is a block diagram illustrating a configuration of a shift detecting device according to a first embodiment of the present disclosure;

FIG. 6 is a flowchart for explaining shift detection processing performed by a shift detecting unit according to the first embodiment; and FIG. 7 is a block diagram illustrating a configuration of a shift detecting system according to a second embodiment of the present disclosure.

DESCRIPTION OF EMBODIMENTS

Basic Idea of Disclosure

Figure 2:
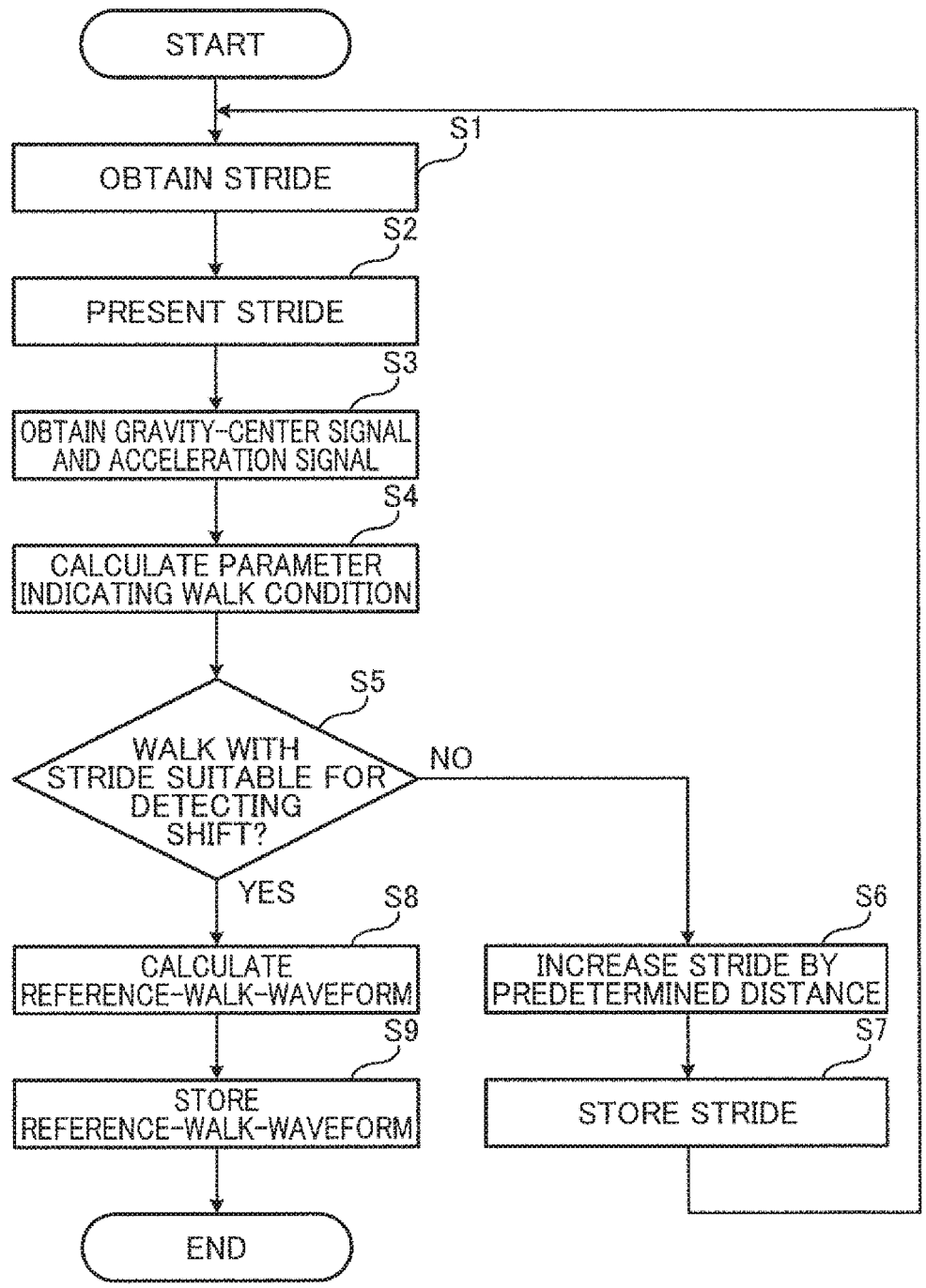
FIG. 2 is a flowchart for explaining reference-walk-waveform generation processing performed by a reference-walk-waveform generating unit according to the first embodiment.

In both JP 2010-259469 A and JP 2013-244055 A, a shift of an attached position of a sensor occurred during a walking motion is detected. It is however difficult to obtain reproducible data from the walking motion of a person because there might be an imbalance between the left and right legs and weakening of muscles due to aging. That is, a shift of the position of the sensor may not be detected accurately from the walking motion.

To solve the problem described above, a detecting method according to one embodiment of the present disclosure is performed by a computer and the computer obtains a first body motion signal from a body motion sensor while a person walks with a predetermined stride, the body motion sensor being attached to a body of the person and configured to detect a body motion of the person, obtains a reference-walk-waveform from a memory, the reference-walk-waveform being generated from a second body motion signal obtained from the body motion sensor while the person walks with the predetermined stride with the body motion sensor attached to an initially attached position, compares the obtained reference-walk-waveform with a waveform of the obtained first body motion signal to determine whether an attached position of the body motion sensor is shifted from the initially attached position, and outputs a determination result.

In this configuration, the waveform of a first body motion signal that is obtained from the body motion sensor attached to the body of a person to detect the body motion of the person while the person walks with a predetermined stride is compared with the reference-walk-waveform that is generated from the second body motion signal obtained from the body motion sensor while the person walks with the predetermined stride with the body motion sensor attached to the initially attached position. When the person walks with the predetermined stride with the body motion sensor attached to the same position as the initially attached position, the waveform of the first body motion signal is substantially identical to the waveform of the reference-walk-waveform. When the person walks with the predetermined stride with the body motion sensor attached to a position shifted from the initially attached position, the waveform of the first body motion signal is not substantially identical to the reference-walk-waveform. It can be determined that the attached position of the body motion sensor is the same as the initially attached position when the waveform of the first body motion signal is similar to the reference-walk-waveform, and it can be determined that the attached position of the body motion sensor is shifted from the initially attached position when the waveform of the first body motion signal is not similar to the reference-walk-waveform. Thus, the shift of the attached position of the body motion sensor from the initially attached position can be detected with high accuracy from the walking motion of the person.

The detecting method described above may further include obtaining, while the person walks with the body motion sensor attached to the initially attached position, the second body motion signal from the body motion sensor, determining whether the person is walking with the predetermined stride from which whether the attached position of the body motion sensor is shifted from the initially attached position can be determined, generating, when it is determined that the person is walking with the predetermined stride, a reference-walk-waveform from the second body motion signal obtained from the body motion sensor, and storing the generated reference-walk-waveform in the memory.

In this configuration, when it is determined that the person is walking with a stride from which whether the attached position of the body motion sensor is shifted from the initially attached position can be determined, the reference-walk-waveform is generated from the second body motion signal obtained from the body motion sensor and the generated reference-walk-waveform is stored in the memory. As the person walks with the predetermined stride after the reference-walk-waveform has been stored in the memory, whether the attached position of the body motion sensor is shifted from the initially attached position can surely be determined using the first body motion signal obtained from the body motion sensor and the reference-walk-waveform stored in the memory.

In the detecting method described above, the body motion sensor may be configured to detect an acceleration of the body of the person and output an acceleration signal, and the method may further include calculating a walk condition including at least one of a maximum value of the acceleration, a stride of the person, and a walk cycle of the person based on the acceleration signal obtained from the body motion sensor, and whether the person is walking with the predetermined stride may be determined based on the calculated walk condition.

In this configuration, whether the person is walking with the predetermined stride can be determined using the walk condition including at least one of the maximum value of acceleration, the stride of the person, and the walk cycle of the person calculated from the acceleration signal obtained from the body motion sensor.

In the detecting method described above, the body motion sensor is configured to detect an acceleration of the body of the person and output an acceleration signal, and the method may further include obtaining a gravity-center signal from a pressure sensor that detects a change in a gravity center of the person while the person walks, and calculating a walk condition including at least one of a maximum value of the acceleration, a stride of the person, and a walk cycle of the person based on the acceleration signal obtained from the body motion sensor and the gravity-center signal obtained from the pressure sensor, and whether the person is walking with the predetermined stride may be determined based on the calculated walk condition.

In this configuration, the walk condition including at least one of the maximum value of acceleration, the stride of the person, and the walk cycle of the person can be calculated correctly based on the acceleration signal obtained from the body motion sensor, which detects the acceleration of the body of the person, and the gravity-center signal obtained from the pressure sensor, which detects the change in the gravity center of the person, and therefore whether the person is walking with the predetermined stride can surely be determined using the calculated walk condition.

In the detecting method described above, at least one of a standard deviation of the calculated maximum value of the acceleration, a standard deviation of the stride of the person, and a standard deviation of the walk cycle of the person is calculated, and it is determined that the person is walking with the predetermined stride when at least one of the calculated standard deviation of the maximum value of the acceleration, the standard deviation of the stride, and the standard deviation of the walk cycle is below a threshold value.

In this configuration, it can be determined that the person is walking more likely with the predetermined stride when the variation of the maximum value of acceleration, the variation of the stride of the person, and the variation of the walk cycle are smaller. Thus, when at least one of the calculated standard deviation of the maximum value of acceleration, the standard deviation of the stride, and the standard deviation of the walk cycle is below the threshold, it can surely be determined that the person is walking with the predetermined stride.

In the detecting method described above, the reference-walk-waveform may be generated by averaging a plurality of body motion signals cut out from the second body motion signal at every walk cycle.

In this configuration, the reference-walk-waveform for a single walk cycle is generated by calculating the average of a plurality of body motion signals cut out from the second body motion signal at every walk cycle.

The detecting method described above may further include storing the predetermined stride in the memory when it is determined that the person is walking with the predetermined stride, and presenting, before obtaining the first body motion signal, the predetermined stride stored in the memory to the person to instruct the person to walk with the predetermined stride.

In this configuration, the predetermined stride stored in the memory is presented to the person and the person keeps walking with the presented predetermined stride, so that the shift of the attached position of the body motion sensor from the initially attached position can be detected from the walking motion of the person with high accuracy.

In the detecting method described above, it may be determined that the attached position of the body motion sensor is shifted from the initially attached position when at least one of differences, regarding a walk cycle, a stride, and a maximum value, between the reference-walk-waveform and the waveform of the obtained first body motion signal is equal to or higher than a threshold.

In this configuration, whether at least one of the differences, regarding the walk cycle, the stride, and the maximum value, between the reference-walk-waveform and the waveform of the obtained first body motion signal is equal to or higher than the threshold is determined, so that whether the attached position of the body motion sensor is shifted from the initially attached position can easily be determined.

In the detecting method described above, the body motion sensor may be attached to an ankle of the person.

In this configuration, the body motion sensor is attached to an ankle of the person, so that the body motion made in the walking motion of the person can be detected by the body motion sensor with high accuracy.

A detecting device according to another aspect of the present disclosure includes a processor and a memory, and the processor obtains a first body motion signal from the body motion sensor while a person walks with a predetermined stride, the body motion sensor being attached to a body of the person and configured to detect a body motion of the person, obtains a reference-walk-waveform from the memory, the reference-walk-waveform being generated from the second body motion signal obtained from the body motion sensor while the person walks with the predetermined stride with the body motion sensor attached to an initially attached position, compares the obtained reference-walk-waveform with the waveform of the obtained first body motion signal to determine whether an attached position of the body motion sensor is shifted from the initially attached position, and outputs a determination result.

In this configuration, the waveform of the first body motion signal that is obtained from the body motion sensor attached to the body of the person to detect the body motion of the person while the person walks with the predetermined stride is compared with the reference-walk-waveform that is generated from the second body motion signal obtained from the body motion sensor while the person walks with the predetermined stride with the body motion sensor attached to the initially attached position. When the person walks with the predetermined stride with the body motion sensor attached to the same position as the initially attached position, the waveform of the first body motion signal is substantially identical to the waveform of the reference-walk-waveform. When the person walks with the predetermined stride with the body motion sensor attached to a position shifted from the initially attached position, the waveform of the first body motion signal is not substantially identical to the reference-walk-waveform. It can be determined that the attached position of the body motion sensor is the same as the initially attached position when the waveform of the first body motion signal is similar to the reference-walk-waveform, and it can be determined that the attached position of the body motion sensor is shifted from the initially attached position when the waveform of the first body motion signal is not similar to the reference-walk-waveform. Thus, the shift of the attached position of the body motion sensor from the initially attached position can be detected with high accuracy from the walking motion of the person.

A detecting system according to another aspect of the present disclosure includes the body motion sensor, and the detecting device.

In this configuration, the waveform of the first body motion signal that is obtained from the body motion sensor attached to the body of the person to detect the body motion of the person while the person walks with the predetermined stride is compared with the reference-walk-waveform that is generated from the second body motion signal obtained from the body motion sensor while the person walks with the predetermined stride with the body motion sensor attached to the initially attached position. When the person walks with the predetermined stride with the body motion sensor attached to the same position as the initially attached position, the waveform of the first body motion signal is substantially identical to the waveform of the reference-walk-waveform. When the person walks with the predetermined stride with the body motion sensor attached to a position shifted from the initially attached position, the waveform of the first body motion signal is not substantially identical to the reference-walk-waveform. It can be determined that the attached position of the body motion sensor is the same as the initially attached position when the waveform of the first body motion signal is similar to the reference-walk-waveform, and it can be determined that the attached position of the body motion sensor is shifted from the initially attached position when the waveform of the first body motion signal is not similar to the reference-walk-waveform. Thus, the shift of the attached position of the body motion sensor from the initially attached position can be detected with high accuracy from the walking motion of the person.

Embodiments of the present disclosure will be described with reference to the attached drawings. The embodiments described below are specific examples for embodying the present disclosure and thus do not limit the technical scope of the present disclosure.

First Embodiment

Figure 1:
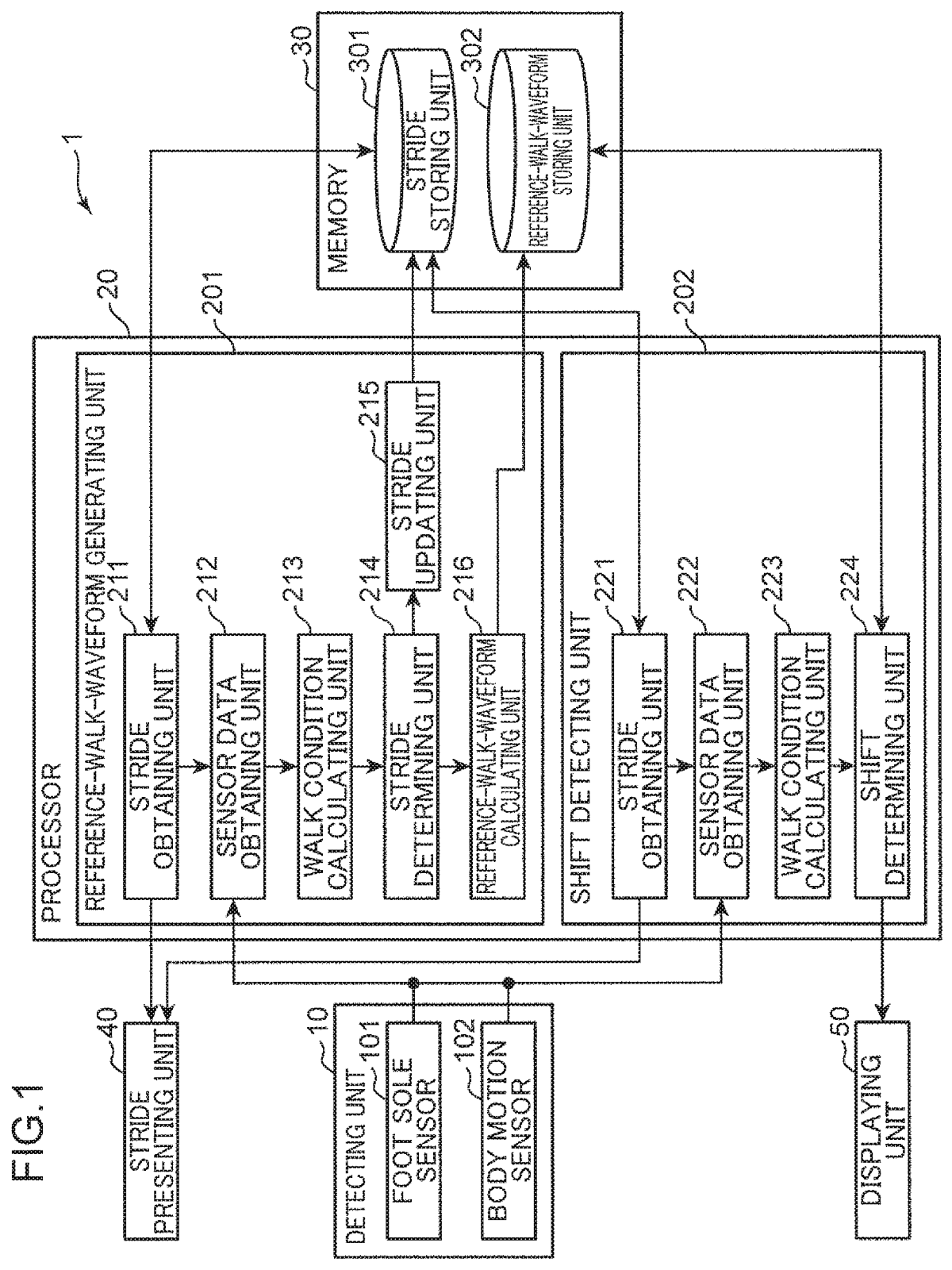

A shift detecting device according to a first embodiment will be described based on FIG. 1.

FIG. 1 is a block diagram illustrating a configuration of a shift detecting device according to the first embodiment of the present disclosure. A shift detecting device 1 according to the first embodiment includes a detecting unit 10, a processor 20, a memory 30, a stride presenting unit 40, and a displaying unit 50.

The detecting unit 10 detects a force that acts on a foot sole as well as a movement of the body of a person.

First, the detecting unit 10 will be described in detail. The detecting unit 10 includes a foot sole sensor 101 and a body motion sensor 102.

The foot sole sensor 101 detects a force that acts on the foot sole when a person walks. The body motion sensor 102 detects a body motion while the person walks. For example, a known foot switch can be used as the foot sole sensor 101. For example, a known posture sensor can be used as the body motion sensor 102.

The foot switch includes a film pressure sensor to measure the walk cycle by the foot sole making contact with the ground. The foot switch can detect as values the change in the gravity center from the pressure that acts on the foot sole while the person walks. In this manner, the foot sole sensor 101 detects the change in the gravity center of the walking person and outputs a gravity-center signal while the person walks.

The body motion sensor 102 detects an acceleration of the body of the person and outputs an acceleration signal. Since the posture sensor typically includes, for example, a three-axis accelerometer, a three-axis gyro (for measuring angular velocities), and a three-axis magnetic sensor (for measuring angular displacements), the acceleration along and the rotating angle about each of the up, down, right, left, forward, and rearward directions of the body of the person can be measured by a single sensor.

The foot sole sensor 101 may output raw data as it is, or perform calibration processing on the raw data including an offset and output the resulting data. To reduce the effect of differences in body weight and the gravity center acting on a foot among users, it is preferable to instruct the person to perform a walking motion in advance with the foot sole sensor 101 attached to check if there is any shift of the foot sole sensor 101 from the attached position.

The foot sole sensor 101 may be attached to any position as long as the foot sole sensor 101 contacts the foot sole while the person walks. The foot sole sensor 101 may be provided on a shoe sole or an insole placed inside a shoe. In particular, the foot sole sensor 101 is preferably provided near a heel portion which contacts the foot sole while the person walks. The foot sole sensor 101 attached to the heel portion can surely detect the pressure that acts when the foot sole comes in contact. For example, when the tot sole sensor 101 is attached near an arch of a foot, the pressure might not be detected while the person walks. Attaching the foot sole sensor 101 to the heel portion has an advantage of measuring how the foot sole comes in contact with high accuracy.

The body motion sensor 102 may be an acceleration sensor or an angular velocity sensor attached to a terminal device, such as a smartphone and a tablet. The body motion sensor 102 needs not output raw data as it is but may perform calibration processing on the raw data regarding an offset or sensitivity and output the calibrated data. Calibration processing regarding temperature compensation may be performed by the body motion sensor 102 using the temperature measured by the temperature sensor additionally embedded in the detecting unit 10.

Any acceleration sensor having a single, two, or three axes may be used as the acceleration sensor. It is preferable to use a three-axis acceleration sensor that detects, while the person walks, accelerations in three directions, namely, the vertical direction, the horizontal front-and-rear direction, and the horizontal right-and-left direction. The acceleration sensor however is not limited to a three-axis acceleration sensor.

The position where the body motion sensor 102 is attached is not particularly limited. The body motion sensor 102 is preferably attached to a portion of the trunk of the person near a belt or attached to an ankle or a thigh with a belt wound around the ankle or the thigh. More preferably, the body motion sensor 102 is attached to the waist or a foot so that a cyclic motion of walking can be detected. If the body motion sensor 102 is to be attached to the ankles, the body motion sensor 102 may be attached only to one of the ankles. In the first embodiment, the body motion sensor 102 is attached to the front portion of an ankle. The body motion sensor 102 may be attached to the body by sticking onto a shoe or clothes that the user wears (such as pants or a sock), by embedding in a shoe or clothes, or by clipping onto a sock or a clothes using a clips. By attaching the body motion sensor 102 to such a position described above, an acceleration and a rotational angle can be measured under a small external disturbance (changes caused by walking or a motion other than walking). In this manner, the acceleration and the rotational angle of the body of the person can advantageously be measured accurately.

A transmitting unit that transmits data by a wireless-communication system or by a wired-communication system is preferably embedded in the foot sole sensor 101 and the body motion sensor 102. In such a case, it may be configured that only the foot sole sensor 101 transmits data wirelessly and the body motion sensor 102 is integrated with the shift detecting device 1 or both the foot sole sensor 101 and body motion sensor 102 each transmits data wirelessly.

In the first embodiment, a detecting unit 10 of the shift detecting device 1 may include only the body motion sensor 102 and not include the foot sole sensor 101.

A processor 20 includes a reference-walk-waveform generating unit 201 and a shift detecting unit 202. The memory 30 includes a stride storing unit 301 and a reference-walk-waveform storing unit 302. The memory 30 is a storing device that can store various types of information, such as a Random Access Memory (RAM), a Hard Disk Drive (HDD), a Solid State Drive (SSD), and a flash memory.

The reference-walk-waveform generating unit 201 will now be described in detail.

The reference-walk-waveform generating unit 201 estimates the walk condition of the person, specifically, the walk cycle and the moved distance (for example, a stride), based on a signal from the detecting unit 10.

The reference-walk-waveform generating unit 201 includes a stride obtaining unit 211, a sensor data obtaining unit 212, a walk condition calculating unit 213, a stride determining unit 214, a stride updating unit 215, and a reference-walk-waveform calculating unit 216.

The reference-walk-waveform generating unit 201 performs processing of determining the initially attached position of the body motion sensor 102 of the detecting unit 10. For example, the reference-walk-waveform generating unit 201 performs the processing when the body motion sensor 102 is attached.

The stride storing unit 301 stores a predetermined stride suitable for detecting a shift. The stride storing unit 301 may store a present-pattern suitable for detecting a shift.

The stride obtaining unit 211 obtains the stride stored in the stride storing unit 301. The stride obtaining unit 211 generates a present-pattern of the obtained stride and outputs the present-pattern to the stride presenting unit 40. If the stride obtaining unit 211 obtains the present-pattern from the stride storing unit 301, the stride obtaining unit 211 outputs the obtained present-pattern of the stride to the stride presenting unit 40.

The stride presenting unit 40 presents the stride obtained from the stride obtaining unit 211 to instruct the user to walk with the predetermined stride. The stride presenting unit 40 may be a speaker that presents the stride by a voice or a buzzing sound. The stride presenting unit 40 may include, for example, a laser light source to emit a laser light to a targeted place, determined by the stride, where a foot is to be moved forward. If the laser light is used, the stride presenting unit 40 may be controlled to emit the laser light when the foot sole is in contact with the ground (during a period in the walk cycle when the body is supported by a leg). The stride presenting unit 40 may inform the user of the specific length of the stride by a character or an image. The stride presenting unit 40 may be a light emitting unit, such as a light emitting diode (LED). For example, the stride presenting unit 40 may have at least either of the visually presenting function and the auditory presenting function described above.

As a pattern of presenting the targeted place where the foot is to be moved forward, for example, the stride presenting unit 40 first inform the user by a sound so that the user can move a foot at the timing same as the timing when a buzzing sound is emitted. The stride presenting unit 40 may output a buzzing sound at every second after 0.5 seconds has elapsed after giving information by a voice guidance, thereby presenting the timing of moving forward a foot. The timing of outputting a buzzing sound corresponding to the stride may previously be stored in the stride storing unit 301. The buzzing sound is output at a predetermined time interval. Specifically, a typical walking motion of a person is made with a cycle of about 0.3 to 1.6 seconds per each stride, namely, within a cyclic range from 0.7 Hz to 3.0 Hz. The time interval for outputting a buzzing sound may be determined within such a cyclic range.

The sensor data obtaining unit 212 obtains a signal from the detecting unit 10 and performs data processing using, for example, a low-pass filter, on the signal to remove noise. Sensor data can be received by a wireless-communication system or a wired-communication system. In this case, the sensor data obtaining unit 212 receives sensor data by a communication system capable of receiving the sensor data. The cut-off frequency of the low-pass filter is preferably from 4 Hz to 10 Hz. If the body motion sensor 102 is a three-axis acceleration sensor, the sensor data obtaining unit 212 may calculate a synthesized acceleration expressed by equation (1) listed below from signals X, Y, and Z of the three-axis acceleration sensor.

$$\text{Synthesized acceleration} = (X^2 + Y^2 + Z^2)^{1/2} \qquad (1)$$

The sensor data obtaining unit 212 measures, for example, a body motion signal with a predetermined sampling frequency (for example, 100 Hz). Any sampling frequency that can follow the body motion velocity can be used for measuring the body motion. For example, the sampling frequency is preferably within the range from 10 to 1000 Hz.

The sensor data obtaining unit 212 obtains a body motion signal (second body motion signal) that the body motion sensor 102 obtains while the person walks with the body motion sensor 102 attached to the initially attached position. The sensor data obtaining unit 212 obtains a gravity-center signal that the foot sole sensor 101, which detects the change in the gravity center of the person, obtains while the person walks.

Based on the signal obtained from the sensor data obtaining unit 212, the walk condition calculating unit 213 calculates the walk cycle and the stride of the person with the body motion sensor 102 attached. Based on the acceleration signal obtained from the body motion sensor 102 and the gravity-center signal obtained from the foot sole sensor 101, the walk condition calculating unit 213 calculates the walk condition including at least one of the maximum value of acceleration, the stride of the person, and the walk cycle of the person. Based on the acceleration signal obtained from the body motion sensor 102, the walk condition calculating unit 213 may calculate the walk condition including at least one of the maximum value of acceleration, the stride of the person, and the walk cycle of the person.

To calculate the walk cycle from the signal from the foot sole sensor 101 obtained by the sensor data obtaining unit 212, for example, the walk condition calculating unit 213 takes the point of time when the signal exceeds a threshold value (when one of feet contacts the ground) as a reference and calculates the time period from the reference to the point of time when the signal exceeds the threshold value the next time (when the foot moved forward contacts the ground again) as one walk cycle (the time it takes for one walk cycle). To calculate the walk cycle from the signal from the body motion sensor 102, which is an acceleration sensor, for example, the walk condition calculating unit 213 detects as a feature quantity the maximum peak value in the vertical direction that is generated at the timing of the heel contacting the ground, calculates the time period of the zone between the point of times when the feature quantity is detected, and determines the time period as one walk cycle. The walk condition calculating unit 213 may calculate the walk cycle using either of the methods but uses at least either one of the methods to calculate the walk cycle.

As for the method of calculating the stride, the walk condition calculating unit 213 may estimate the stride from the signal from the body motion sensor 102 by integrating the acceleration in the moving direction (front-and-rear direction). Simply integrating the acceleration however might cause a drift. For this reason, the walk condition calculating unit 213 calculates a regression curve for the integrated result of acceleration and subtracts the value of the calculated regression curve from the integrated result to calculate a relative stride. The walk condition calculating unit 213 may calculate the area of the relative stride corresponding to the interval of the walk cycle calculated from the signals from the foot sole sensor 101 as the stride.

The walk condition calculating unit 213 may estimate the walk velocity by calculating the walk frequency from the body motion signal. In this case, the walk condition calculating unit 213 performs one-dimensional discrete Fourier transform processing on the body motion signal to estimate as the walk velocity (walk frequency) the frequency of the component that has the maximum power in the data range that has been transformed into a frequency region. The walk condition calculating unit 213 may calculate the walk velocity from the walk cycle and the stride described above.

The parameter indicating the walk condition calculated by the walk condition calculating unit 213 may be at least one of the maximum value of acceleration, the walk cycle, the stride, and the walk velocity.

The signal obtained during walking is divided into chronologically suitable length. There is no limitation on the length as long as a targeted signal is continuously included in the length. It is preferable that several cycles of the targeted signal are included within the length if the walking motion is cyclically repeated. For a walking motion, for example, it is preferable that the signal has the length of about 5 to 10 seconds.

The stride determining unit 214 determines whether the person is walking with the predetermined stride from which whether the attached position of the body motion sensor 102 is shifted from the initially attached position can be determined. Based on the walk condition calculated by the walk condition calculating unit 213, the stride determining unit 214 determines whether the person is walking with the predetermined stride.

Based on the parameter indicating the walk condition calculated by the walk condition calculating unit 213, the stride determining unit 214 determines whether the person is walking with a predetermined stride suitable for detecting a shift. The parameter indicating the walk condition is at least one of the walk cycle, the stride, and the maximum value of acceleration. For example, if a pattern having a distinguishing and large amplitude suddenly appears when the person walks at a constant cycle, the stride determining unit 214 regards that the walk condition has changed and determines that the person is walking in an unsuitable manner, namely, with a stride different from the predetermined stride.

Note that, the stride determining unit 214 may calculate the average or the degree of variation of the parameter indicating the walk condition, such as the walk cycle and the stride, and if the average value or the variation exceeding the predetermined threshold that has previously been set is detected for the several walk cycles, the stride determining unit 214 determines that the person is walking in an unsuitable manner, namely, with a stride different from the predetermined stride. To improve the accuracy of this determination, the stride determining unit 214 may correct the parameter indicating the walk condition for the person who actually wears the stride determining unit 214 according to the predetermined standard of determination. The stride determining unit 214 may calculate the standard deviation to express the degree of variation of the parameter indicating the walk condition or may change the threshold according to the age or the height of the person wearing the stride determining unit 214. Every one or at least one of the change in the gravity center, the stride, and the walk cycle may be used to determine whether the person is walking with the predetermined stride suitable for detecting a shift.

The stride determining unit 214 calculates at least one of the standard deviation of the calculated maximum value of acceleration, the standard deviation of the stride of the person, and the standard deviation of the walk cycle of the person and if at least one of the calculated standard deviation of the maximum value of acceleration, the standard deviation of the stride, and the standard deviation of the walk cycle is below the a threshold value, the stride determining unit 214 determines that the person is walking with the predetermined stride.

If the stride determining unit 214 determines that the person is not walking with the predetermined stride, the stride updating unit 215 changes the stride stored in the stride storing unit 301. The stride updating unit 215 increases the current stride stored in the stride storing unit 301 to be longer by a predetermined length. The stride obtaining unit 211 obtains the stride updated by the stride updating unit 215 and outputs the updated stride to the stride presenting unit 40. The stride presenting unit 40 presents the stride updated by the stride updating unit 215. Then, the person walks with the newly presented stride. The stride updating unit 215 changes the stride stored in the stride storing unit 301 until it is determined that the person is walking with the predetermined stride from which whether the attached position of the body motion sensor 102 is shifted from the initially attached position can be determined. On determining that the person is walking with the predetermined stride, the stride determining unit 214 stores the predetermined stride in the stride storing unit 301.

If the stride determining unit 214 determines that the person is not walking with the predetermined stride, the stride updating unit 215 may change the pattern of the predetermined time interval for presenting the stride to a pattern of a different time interval. The patterns each have a predetermined value range of time interval and are set stepwise, and the setting may suitably be changed for each user.

If it is determined that the person is walking with the predetermined stride, the reference-walk-waveform calculating unit 216 generates the reference-walk-waveform from the body motion signal (second body motion signal) obtained from the body motion sensor 102. The reference-walk-waveform calculating unit 216 calculates the average of a plurality of body motion signals cut out from the body motion signal (second body motion signal) every walk cycle to generate the reference-walk-waveform. The reference-walk-waveform calculating unit 216 calculates the reference-walk-waveform by, for example, averaging the body motion signals obtained while the person walks with the stride suitable for detecting a shift. In this case, the reference-walk-waveform calculating unit 216 may calculate the average for a plurality of body motion signals which are cut out at every walk cycle and chronologically adjusted with the peak value.

The reference-walk-waveform storing unit 302 stores the reference-walk-waveform of the body motion signal including time information calculated by the reference-walk-waveform calculating unit 216. The reference-walk-waveform calculating unit 216 stores the generated reference-walk-waveform in the reference-walk-waveform storing unit 302.

Now, the shift detecting unit 202 will be described in detail.

The shift detecting unit 202 instructs the user to walk in a cyclic manner based on the stride determined by the reference-walk-waveform generating unit 201, and determines whether the attached position of the body motion sensor 102 is shifted from the initially attached position based on the reference-walk-waveform generated by the reference-walk-waveform generating unit 201.

If the attached position of the body motion sensor 102 is shifted from the initially attached position while the person walks with the stride which is determined by the reference-walk-waveform generating unit 201 and suitable for detecting a shift, the shift detecting unit 202 detects the shift of the attached position of the body motion sensor 102.

The shift detecting unit 202 includes a stride obtaining unit 221, a sensor data obtaining unit 222, a walk condition calculating unit 223, and a shift determining unit 224.

The stride obtaining unit 221 obtains the stride stored in the stride storing unit 301. The stride obtaining unit 221 generates a present-pattern of the obtained stride and outputs the present-pattern to the stride presenting unit 40. If the stride obtaining unit 221 obtains the present-pattern of the stride from the stride storing unit 301, the stride obtaining unit 221 outputs the obtained present-pattern of the stride to the stride presenting unit 40. The stride obtaining unit 221 has the same function as the stride obtaining unit 211. The stride presenting unit 40 presents the stride obtained by the stride obtaining unit 221 to instruct the user to walk with the predetermined stride. The person with the body motion sensor 102 attached walks with the cycle instructed by the present-pattern given by the stride presenting unit 40. That is, the stride presenting unit 40 presents the predetermined stride stored in the stride storing unit 301 to the person to instruct the person to walk with the predetermined stride before the sensor data obtaining unit 222 obtains the body motion signal (first body motion signal).

While the person walks with the predetermined stride, the sensor data obtaining unit 222 obtains the body motion signal (first body motion signal) from the body motion sensor 102 that is attached to the body of the person to detect the body motion of the person.

The sensor data obtaining unit 222 obtains a signal from the detecting unit 10 and performs data processing, for example, using a low-pass filter, on the signal to remove noise. Sensor data can be received by a wireless-communication system or a wired-communication system. In this case, the sensor data obtaining unit 222 receives the sensor data by a communication system capable of receiving the sensor data. If the body motion sensor 102 is a three-axis acceleration sensor, the sensor data obtaining unit 222 may calculate a synthesized acceleration expressed by equation (1) listed above from the signals X, Y, and Z of the three-axis acceleration sensor. The sensor data obtaining unit 222 has the same function as the sensor data obtaining unit 212.

The walk condition calculating unit 223 divides by the walk cycle the acceleration signal from the body motion sensor 102 obtained by the sensor data obtaining unit 222. Specifically, the walk condition calculating unit 223 detects the maximum peak value in the vertical direction occurring at a timing when the heel contacts the ground as the feature quantity and calculates the interval between the detected two maximum peak values as one walk cycle. The walk condition calculating unit 223 may calculate the walk cycle using the gravity-center signal from the foot sole sensor 101 and divide the acceleration signal by the walk cycle. The walk condition calculating unit 223 cuts out a waveform of one walk cycle of the acceleration signal from the acceleration signal divided by the walk cycle, and outputs the cut out waveform of one walk cycle of the acceleration signal to the shift determining unit 224.

The shift determining unit 224 obtains from the reference-walk-waveform storing unit 302 the reference-walk-waveform generated from the body motion signal (second body motion signal) obtained from the body motion sensor 102 while the person walks with the predetermined stride with the body motion sensor 102 attached to the initially attached position. The shift determining unit 224 compares the obtained reference-walk-waveform with the waveform of the body motion signal (first body motion signal) obtained from the body motion sensor 102 and determines whether the attached position of the body motion sensor 102 is shifted from the initially attached position.

If the differences, regarding the walk cycle, the stride, and the maximum value of the reference-walk-waveform, between the reference-walk-waveform and the waveform of the obtained body motion signal (first body motion signal) are equal to or higher than the respective thresholds, the shift determining unit 224 determines that the attached position of the body motion sensor 102 is shifted from the initially attached position.

The shift determining unit 224 may determine that the attached position of the body motion sensor 102 is shifted from the initially attached position if at least one of the differences, regarding the walk cycle, the stride, and the maximum value of the reference-walk-waveform, between the reference-walk-waveform and the waveform of the obtained body motion signal (first body motion signal) is equal to or higher than the threshold.

The shift determining unit 224 evaluates whether there is a shift between the reference-walk-waveform stored in the reference-walk-waveform storing unit 302 and the waveform of one walk cycle of the body motion signal calculated by the walk condition calculating unit 223.

The shift determining unit 224 may determine whether the maximum peak value of the acceleration signal calculated by the walk condition calculating unit 223 is within a predetermined range based on the maximum peak value of the reference-walk-waveform of the averaged acceleration signal stored in the reference-walk-waveform storing unit 302. The shift determining unit 224 may determine whether the stride of the acceleration signal calculated by the walk condition calculating unit 223 is within a predetermined range based on the stride of the reference-walk-waveform of the averaged acceleration signal stored in the reference-walk-waveform storing unit 302. The shift determining unit 224 may determine whether the walk cycle of the acceleration signal calculated by the walk condition calculating unit 223 is within a predetermined range based on the walk cycle of the reference-walk-waveform of the averaged acceleration signal stored in the reference-walk-waveform storing unit 302.

If the shift determining unit 224 determines that the maximum peak value of the acceleration signal calculated by the walk condition calculating unit 223 is out of the predetermined range based on the maximum peak value of the reference-walk-waveform, if the stride of the acceleration signal calculated by the walk condition calculating unit 223 is out of the predetermined range based on the stride of the reference-walk-waveform, or if the walk cycle of the acceleration signal calculated by the walk condition calculating unit 223 is out of the predetermined range based on the walk cycle of the reference-walk-waveform, the shift determining unit 224 determines that the attached position of the body motion sensor 102 is shifted.

Meanwhile, the shift determining unit 224 determines that the attached position of the body motion sensor 102 is not shifted if the shift determining unit 224 determines that the maximum peak value of the acceleration signal calculated by the walk condition calculating unit 223 is within the predetermined range based on the maximum peak value of the reference-walk-waveform, the stride of the acceleration signal calculated by the walk condition calculating unit 223 is within the predetermined range based on the stride of the reference-walk-waveform, and the walk cycle of the acceleration signal calculated by the walk condition calculating unit 223 is within the predetermined range based on the walk cycle of the reference-walk-waveform.

The shift determining unit 224 may determine whether at least one of the maximum peak value, the stride, and the walk cycle of the acceleration signal calculated by the walk condition calculating unit 223 is within the respective predetermined ranges respectively based on the maximum peak value, the stride, and the walk cycle of the reference-walk-waveform of the averaged acceleration signal stored in the reference-walk-waveform storing unit 302. If at least one of the maximum peak value, the stride, and the walk cycle of the acceleration signal calculated by the walk condition calculating unit 223 is out of the respective predetermined ranges of the maximum peak value, the stride, and the walk cycle of the reference-walk-waveform, the shift determining unit 224 determines that the attached position of the body motion sensor 102 is shifted. Meanwhile, if at least one of the maximum peak value, the stride, and the walk cycle of the acceleration signal calculated by the walk condition calculating unit 223 is within the respective predetermined ranges of the maximum peak value, the stride, and the walk cycle of the reference-walk-waveform, the shift determining unit 224 determines that the attached position of the body motion sensor 102 is not shifted.

For example, the predetermined range based on the maximum peak value of the reference-walk-waveform is the range between the maximum peak value of the reference-walk-waveform plus −10% of the maximum peak value and the maximum peak value of the reference-walk-waveform plus 10% of the maximum peak value. For example, the predetermined range based on the stride of the reference-walk-waveform is the range between the stride of the reference-walk-waveform plus −10% of the stride and the stride of the reference-walk-waveform plus 10% of the stride. For example, the predetermined range based on the walk cycle of the reference-walk-waveform is the range between the walk cycle of the reference-walk-waveform plus −10% of the walk cycle and the walk cycle of the reference-walk-waveform plus 10% of the walk cycle.

The shift determining unit 224 may calculate a correlation value between the obtained reference-walk-waveform and the waveform of the body motion signal (first body motion signal) obtained from the body motion sensor 102 and determine whether the calculated correlation value is equal to or higher than a predetermined threshold. The shift determining unit 224 may determine that the attached position of the body motion sensor 102 is not shifted from the initially attached position if the shift determining unit 224 determines that the calculated correlation value is equal to or higher than the predetermined threshold, and determine that the attached position of the body motion sensor 102 is shifted from the initially attached position if the shift determining unit 224 determines that the calculated correlation value is smaller than the predetermined threshold.

The shift determining unit 224 outputs the determination result to the displaying unit 50.

The displaying unit 50 informs the determination result made by the shift determining unit 224 to the user. The displaying unit 50 is, for example, a display panel of a type of a liquid crystal or a light emitting element disposed at a position where the user can easily see an image. The displaying unit 50 may be, for example, a wrist watch type liquid crystal display. The user can wear and view the wrist watch type liquid crystal display while walking.

If the shift detecting device 1 is attached to a place which is difficult to be viewed, such as a foot portion, the shift detecting device 1 may include a speaker instead of the displaying unit 50. The speaker may output the determination result given by the shift determining unit 224 by a buzzing sound or a voice-like sound.

Reference-walk-waveform generation processing performed by the reference-walk-waveform generating unit 201 according to the first embodiment will now be described using FIGS. 2 to 5.

Figure 3:
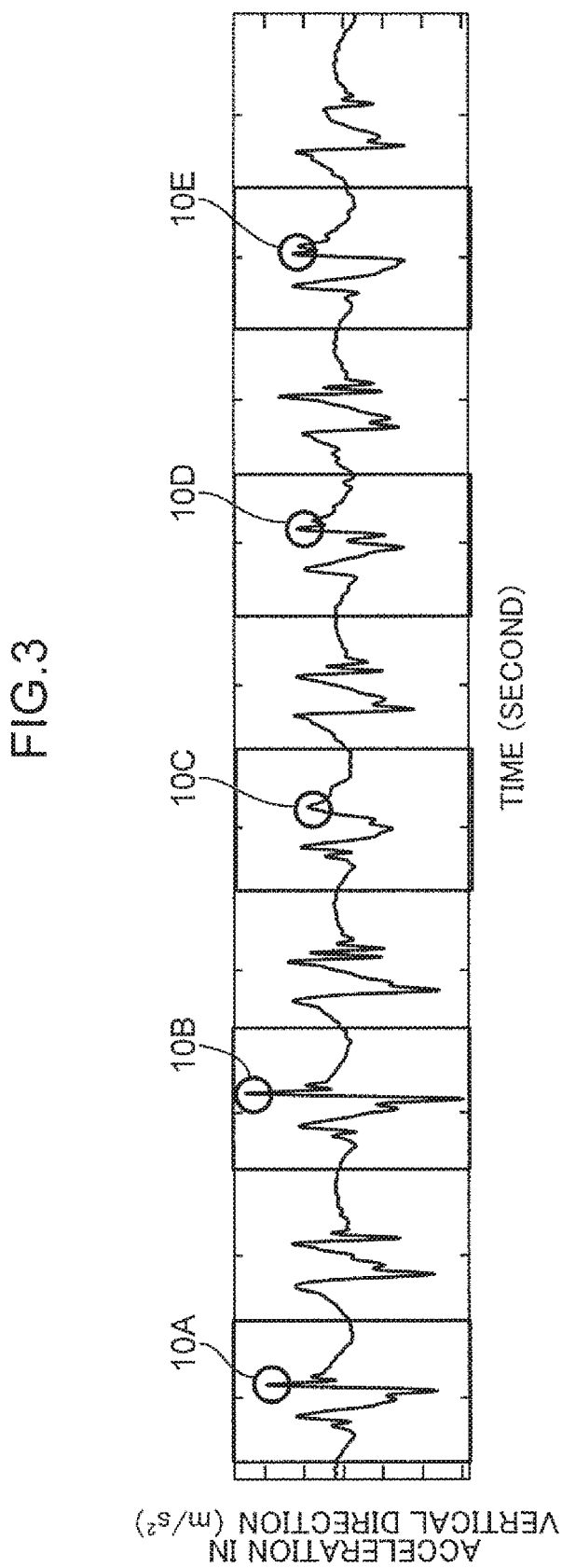
FIG. 3 illustrates a vertical acceleration detected by a body motion sensor while a user walks with a stride of one and a half of the length of a shoe of the user with the body motion sensor attached to a front portion of the right ankle of the user.
Figure 4:
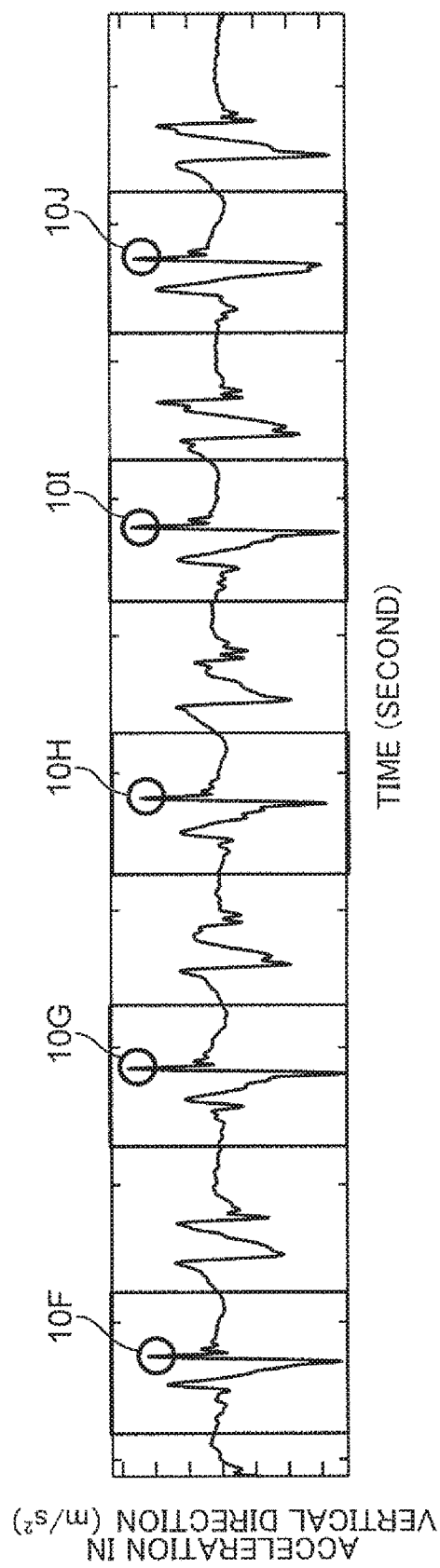
FIG. 4 illustrates a vertical acceleration detected by a body motion sensor while a user walks with a stride of twice the length of the shoe of the user with the body motion sensor attached to the front portion of the right ankle of the user.
Figure 5:
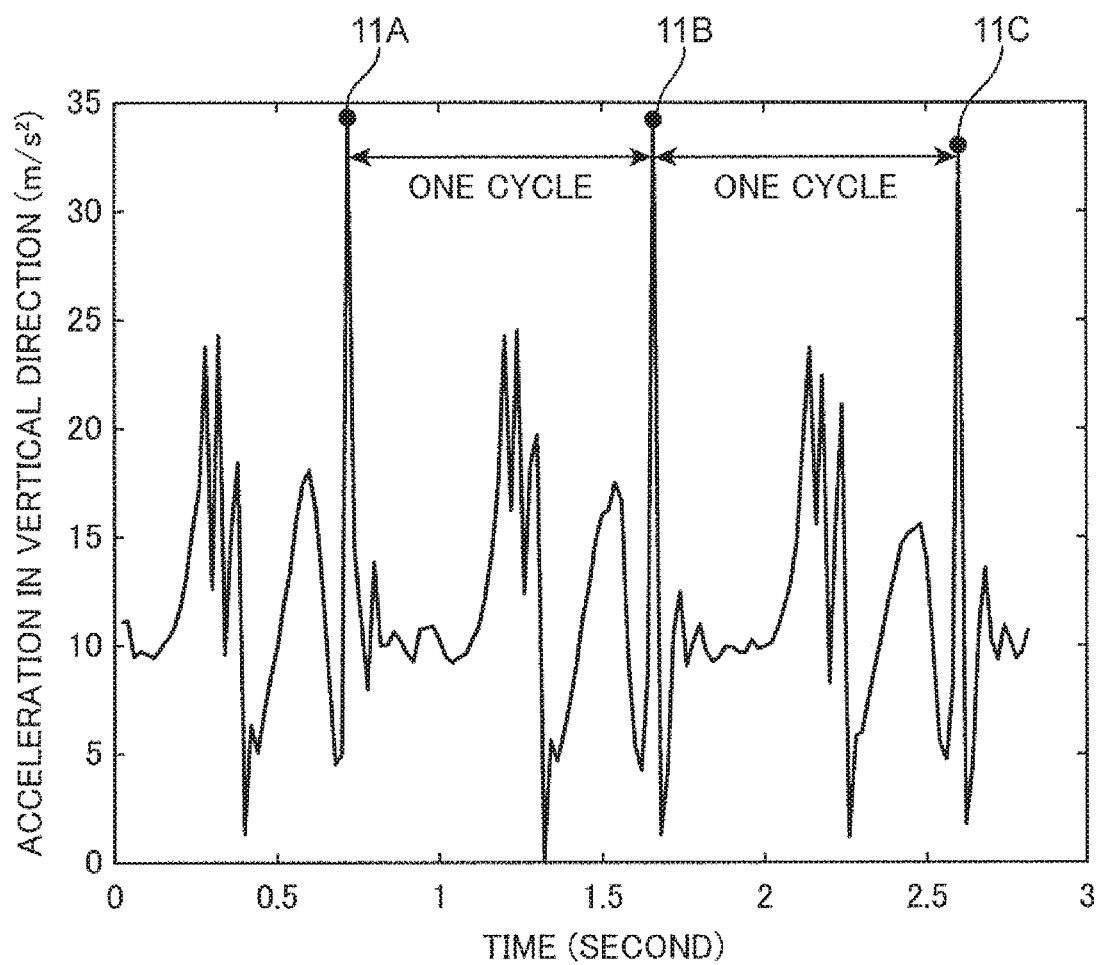
FIG. 5 is a diagram for explaining a method of calculating the reference-walk-waveform in the first embodiment.

FIG. 2 is a flowchart for explaining the reference-walk-waveform generation processing performed by the reference-walk-waveform generating unit according to the first embodiment. FIGS. 3 and 4 are figures for explaining a method of determining a stride suitable for detecting a shift in the first embodiment. FIG. 5 is a diagram for explaining a method of calculating the reference-walk-wave form.

In the reference-walk-waveform generation processing described below, the body motion sensor 102 is an acceleration sensor attached to the front portion of the right ankle and the foot sole sensor 101 is a pressure sensor attached to the heel of the right foot sole. The body motion sensor 102 may be a different sensor, such as an angular velocity sensor, that can detect a body motion signal different from the acceleration signal. The detecting unit 10 may not include both the body motion sensor 102 and foot sole sensor 101 hut may include only the body motion sensor 102. The reference-walk-waveform generation processing starts by an input unit (not shown) receiving an input operation for starting the reference-walk-waveform generation processing. The reference-walk-waveform generation processing may start when a detecting unit (not shown) detects the body motion sensor 102 being attached to the person.

First, in step S1, the stride obtaining unit 211 obtains the stride stored in the stride storing unit 301. The stride storing unit 301 stores in advance an initial stride and a predetermined stride suitable for detecting a shift. The stride obtaining unit 211 obtains the initial stride stored in the stride storing unit 301. The stride obtaining unit 211 outputs a present-pattern corresponding to the obtained stride to the stride presenting unit 40. For example, when the stride is to be presented by a sound, the stride obtaining unit 211 outputs the present-pattern indicating the time interval of outputting the sound according to the stride to the stride presenting unit 40. When the stride is to be presented by a laser light, the stride obtaining unit 211 outputs an angle by which a laser light is emitted and corresponding to the stride to the stride presenting unit 40.

Then, in step S2, the stride presenting unit 40 presents the stride obtained from the stride obtaining unit 211 to the user. The stride presenting unit 40 presents the timing at which the user moves forward a foot by a buzzing sound or a voice-like sound to instruct the user to perform a cyclic walking motion. For example, a time interval at which the buzzing sound is output according to the stride is predetermined, and the stride presenting unit 40 outputs the buzzing sound at every second, for example. The user moves forward a foot at the timing when the buzzing sound is output and thereby performs a cyclic walking motion. The liming of moving forward the foot differs, depending on the stride. If the stride is stored by the stride updating unit 215, the stride obtaining unit 211 reads the stride updated by the stride updating unit 215 and changes the interval of outputting the buzzing sound according to the read stride.

Then, in step S3, the sensor data obtaining unit 212 obtains the gravity-center signal indicating the change in the gravity-center acting on the foot sole from the foot sole sensor 101 as well as the acceleration signal from the body motion sensor 102. The foot sole sensor 101 outputs the gravity-center signal to the sensor data obtaining unit 212, and the body motion sensor 102 outputs the acceleration signal to the sensor data obtaining unit 212. The sensor data obtaining unit 212 outputs the obtained gravity-center signal and the acceleration signal to the walk condition calculating unit 213.

Then, in step S4, the walk condition calculating unit 213 calculates the parameter indicating the walk condition of the person based on the gravity-center signal and the acceleration signal obtained by the sensor data obtaining unit 212. The parameters indicating the walk condition are, for example, the walk cycle, the stride, and the maximum value of acceleration. The walk condition calculating unit 213 calculates the walk cycle, the stride, and the maximum value of acceleration.

A method of calculating the walk cycle, the stride, and the maximum value of acceleration will be described.

The walk condition calculating unit 213 uses the gravity-center signal from the foot sole sensor 101, which detects the chronological change in the pressure while the person walks, to calculate the walk cycle. Specifically, the walk condition calculating unit 213 calculates the time period from the point of time when the gravity-center signal exceeds a predetermined threshold (when the foot sole contacts the ground) to the point of time when the gravity-center signal exceeds the predetermined threshold the next time (when the foot sole contacts the ground the next time as the person walks) as the walk cycle. The predetermined threshold used at the timing of the foot sole contacting the ground is predetermined. Regarding the range for calculating the walk cycle, for example, five walk cycles are calculated if five cycles of steps of one of the feet can be detected in about five seconds.

The walk condition calculating unit 213 calculates the stride. The walk condition calculating unit 213 integrates the acceleration signals from the body motion sensor 102, calculates the regression curve of the integrated result, and subtracts the value of the calculated regression curve from the integrated result. The walk condition calculating unit 213 then integrates the integrated results from which the value of the regression curve has been subtracted, calculated the regression curve of the integrated result, and subtracts the value of the calculated regression curve from the integrated result, thereby obtaining the resulting value of the subtraction as the relative stride. The walk condition calculating unit 213 calculates the stride of each of a plurality of walk cycles, for example, five walk cycles.

The walk condition calculating unit 213 calculates the maximum value of acceleration signal from the body motion sensor 102. The walk condition calculating unit 213 calculates the maximum value of acceleration for each of a plurality of walk cycles, for example, five walk cycles.

In the first embodiment, the walk condition calculating unit 213 calculates the walk cycle, the stride, and the maximum value of acceleration. The present disclosure is not limited to such a configuration. The walk condition calculating unit 213 may calculate at least one of the walk, the stride, and the maximum value of acceleration.

The walk condition calculating unit 213 outputs the parameter indicating the walk condition to the stride determining unit 214.

Then, in step S5, based on the parameter that indicates the walk condition and is calculated by the walk condition calculating unit 213, the stride determining unit 214 determines whether the person is walking with a stride suitable for detecting a shift. The stride determining unit 214 calculates the standard deviation of the maximum value of acceleration of a plurality of cycles, and determines whether the standard deviation of the calculated maximum value of acceleration is below the threshold. The stride determining unit 214 calculates the standard deviation of the walk cycle of a plurality of cycles, and determines whether the calculated standard deviation of the walk cycle is below the threshold. The stride determining unit 214 calculates the standard deviation of the stride of a plurality of cycles, and determines whether the calculated standard deviation of the stride is below the threshold.

The threshold for the standard deviation of the maximum value of acceleration, the threshold for the standard deviation of the walk cycle, and the threshold for the standard deviation of the stride are predetermined.

If the stride determining unit 214 determines that the standard deviation of the maximum value of acceleration is below the threshold, the standard deviation of the walk cycle is below the threshold, and the standard deviation of the stride is below the threshold, the stride determining unit 214 determines that the person is walking in a reproducible manner, namely, the person is walking with the stride suitable for detecting a shift. That is, the stride determining unit 214 determines whether the user is walking in the reproducible manner.

If the stride determining unit 214 determines that the standard deviation of the maximum value of acceleration, the standard deviation of the walk cycle, and the standard deviation of the stride are all below the respective thresholds, the stride determining unit 214 determines that the person is walking with the stride suitable for detecting a shift. Meanwhile, if the stride determining unit 214 determines that at least one of the standard deviation of the maximum value of acceleration, the standard deviation of the walk cycle, and the standard deviation of the stride is equal to or higher than the respective threshold, the stride determining unit 214 determines that the person is not walking with a stride suitable for detecting a shift.

In the first embodiment, the stride determining unit 214 determines that the person is walking with the stride suitable for detecting a shift if the standard deviation of the maximum value of acceleration, the standard deviation of the walk cycle, and the standard deviation of the stride are all below the respective thresholds. The present disclosure is not limited to such a configuration. The stride determining unit 214 may determine that the person is walking with the stride suitable for detecting a shift if any one of the standard deviation of the maximum value of acceleration, the standard deviation of the walk cycle, and the standard deviation of the stride is below the threshold. The stride determining unit 214 may determine that the person is walking with the stride suitable for detecting a shift if any two of the standard deviation of the maximum value of acceleration, the standard deviation of the walk cycle, and the standard deviation of the stride are below the respective thresholds.

If the walk condition calculating unit 213 calculates at least one of the walk cycle, the stride, and the maximum value of acceleration, the stride determining unit 214 may calculate the standard deviation of at least one of the walk cycle, the stride, and the maximum value of acceleration of a plurality of cycles and determine whether at least one of the calculated standard deviations of the walk cycle, the stride, and the maximum value of acceleration is below the threshold.

FIG. 3 illustrates the vertical acceleration detected by the body motion sensor while the user walks with the stride of one and a half of the length of the shoe of the user with the body motion sensor attached to a front portion of the right ankle of the user. FIG. 4 illustrates the vertical acceleration detected by the body motion sensor while the user walks with the stride of twice the length of the shoe of the user with the body motion sensor attached to the front portion of the right ankle of the user. In FIGS. 3 and 4, the vertical axis represents the acceleration in the vertical direction and the horizontal axis represents the time.

In general, the gravity center acts not only on one foot sole when the stride is short. In FIG. 3, the maximum values of acceleration 10A and 10B show the states where the gravity center acts on the right foot and the maximum values of acceleration 10C to 10E show the states where the gravity center acts on the left foot. It means that there is a variation among the maximum values of acceleration 10A to 10E. Thus, it is determined that the standard deviation of the maximum values of acceleration 10A to 10E is equal to or higher than the threshold and that the person is not walking with the stride suitable for detecting a shift.

In contrast, the gravity center acts only on one foot sole if the stride is long. In FIG. 4, the maximum values of acceleration 10F to 10J show the states where the gravity center acts on the right foot. It means that there is no variation among the maximum values of acceleration 10F to 10J. Thus, it is determined that the standard deviation of the maximum values of acceleration 10F to 10J is below the threshold and that the person is walking with the stride suitable for detecting a shift.

If it is determined in step S5 that the person is not walking with a stride suitable for detecting a shift (NO in step S5), the stride updating unit 215 increases the stride by a predetermined distance in step S6. If the time interval of presenting the timing, according to the stride, at which the person moves forward a foot is initially set to one second, the stride updating unit 215 updates the time interval to a longer time interval. For example, the stride updating unit 215 adds 0.5 seconds to the current time interval every time when updating the stride.

Then, in step S7, the stride updating unit 215 stores the updated stride in the stride storing unit 301. The processing returns to step S1, and the stride obtaining unit 211 obtains the stride updated by the stride updating unit 215 from the stride storing unit 301. The stride presenting unit 40 presents the updated stride obtained from the stride obtaining unit 211 to the user.

Meanwhile, if it is determined in step S5 that the person is walking with a stride suitable for detecting a shift (YES in step S5), the reference-walk-waveform calculating unit 216 cuts out the acceleration signal at every walk cycle and calculates the average of the acceleration signal for each walk cycle to calculate the reference-walk-waveform in step S8.

FIG. 5 is a diagram for explaining a method of calculating the reference-walk-waveform in the first embodiment. FIG. 5 illustrates the vertical acceleration detected by the body motion sensor 102 while the user walks with a stride suitable for detecting a shift with the body motion sensor 102 attached to the front portion of the right ankle. In FIG. 5, the vertical axis represents the acceleration in the vertical direction and the horizontal axis represents the time.

The reference-walk-waveform calculating unit 216 detects the peak value that exceeds the threshold when the heel contacts the ground while the person walks, and cuts out the acceleration signal between the detected peak values. Alternatively, the reference-walk-waveform calculating unit 216 detects the maximum value of acceleration in a certain zone and cuts out the acceleration signal obtained in a zone between the detected maximum values. In FIG. 5, the acceleration signal obtained in the zone between the maximum value 11A and the maximum value 11B of acceleration and the acceleration signal obtained between the zone between the maximum value 11B and the maximum value 11C of acceleration are cut out. The reference-walk-waveform calculating unit 216 averages the acceleration signals for each cut out walk cycle to calculate the reference-walk-waveform.

Then, in step S9, the reference-walk-waveform calculating unit 216 stores the calculated reference-walk-waveform in the reference-walk-waveform storing unit 302.

Shift detection processing performed by the shift detecting unit 202 according to the first embodiment will now be described using FIG. 6.

FIG. 6 is a flowchart for explaining the shift detection processing performed by the shift detecting unit according to the first embodiment.

In the shift detection processing described below, the body motion sensor 102 is an acceleration sensor attached to an ankle and the foot sole sensor 101 is a pressure sensor attached to the heel of a foot sole. The body motion sensor 102 may be a different sensor, such as an angular velocity sensor, that can detect a body motion signal. The detecting unit 10 needs nut include a pressure sensor. The shift detection processing starts by the input unit (not shown) receiving an input operation for starting the shift detection processing.

First, in step S21, the stride obtaining unit 221 obtains the stride stored in the stride storing unit 301. The stride obtaining unit 221 outputs the present-pattern corresponding to the obtained stride to the stride presenting unit 40. For example, if the stride is to be presented by a sound, the stride obtaining unit 221 outputs the present-pattern, which indicates the time interval of timings of outputting the sound according to the stride to instruct the user to move forward a foot, to the stride presenting unit 40, if the stride is to be presented by a laser light, the stride obtaining unit 221 outputs an angle, by which the laser light is emitted and corresponding to the stride, to the stride presenting unit 40.

As the timing of the user to move forward a foot is presented by, for example, a buzzing sound, the user is instructed to perform the cyclic walking motion. The stride obtaining unit 221 has the same function as the stride obtaining unit 211.

Then, in step S22, the stride presenting unit 40 presents the stride obtained from the stride obtaining unit 221 to the user. The stride presenting unit 40 presents the timing at which the user moves forward a foot by a buzzing sound or a voice-like sound to instruct the user to perform a cyclic walking motion.

Then, in step S23, the sensor data obtaining unit 222 obtains the gravity-center signal indicating the change in the gravity-center acting on the foot sole from the foot sole sensor 101 as well as the acceleration signal from the body motion sensor 102. The foot sole sensor 101 outputs the gravity-center signal to the sensor data obtaining unit 222, and the body motion sensor 102 outputs the acceleration signal to the sensor data obtaining unit 222. The sensor data obtaining unit 222 outputs the obtained gravity-center signal and the acceleration signal to the walk condition calculating unit 223.

Then, in step S24, the walk condition calculating unit 223 divides the acceleration signal by each walk cycle, and cuts out a waveform of one walk cycle of the acceleration signal from the acceleration signal divided by each walk cycle. The walk condition calculating unit 223 outputs the waveform of the cut out one walk cycle of the acceleration signal to the shift determining unit 224.

Then, in step S25, the shift determining unit 224 obtains the reference-walk-waveform from the reference-walk-waveform storing unit 302.

Then, in step S26, the shift determining unit 224 determines whether the attached position of the body motion sensor 102 is shifted from the initially attached position. Specifically, the shift determining unit 224 calculates the maximum peak value, the stride, and the walk cycle of the reference-walk-waveform obtained from the reference-walk-waveform storing unit 302 and calculates the maximum peak value, the stride, and the walk cycle of the acceleration signal cut out by the walk condition calculating unit 223.

The shift determining unit 224 determines whether the maximum peak value calculated from the waveform of the cut out acceleration signal is within the predetermined range based on the maximum peak value calculated from the reference-walk-waveform. The shift determining unit 224 determines whether the stride calculated from the waveform of the cut out acceleration signal is within the predetermined range based on the stride calculated from the reference-walk-waveform. The shift determining unit 224 determines whether the walk cycle calculated from the waveform of the cut out acceleration signal is within the predetermined range based on the walk cycle calculated from the reference-walk-waveform.

If the shift determining unit 224 determines that the maximum peak value calculated from the waveform of the cut out acceleration signal is out of the predetermined range based on the maximum peak value calculated from the reference-walk-waveform, the shift determining unit 224 determines that the attached position of the body motion sensor 102 is shifted from the initially attached position. Alternatively, if the shift determining unit 224 determines that the stride calculated from the waveform of the cut out acceleration signal is out of the predetermined range based on the stride calculated from the reference-walk-waveform, the shift determining unit 224 determines that the attached position of the body motion sensor 102 is shifted from the initially attached position. Alternatively, if the shift determining unit 224 determines that the walk cycle calculated from the waveform of the cut out acceleration signal is out of the predetermined range based on the walk cycle calculated from the reference-walk-waveform, the shift determining unit 224 determines that the attached position of the body motion sensor 102 is shifted from the initially attached position.

Meanwhile, the shift determining unit 224 determines that the attached position of the body motion sensor 102 is not shifted from the initially attached position if the shift determining unit 224 determines that the maximum peak value calculated from the waveform of the cut out acceleration signal is within the predetermined range based on the maximum peak value calculated from the reference-walk-waveform, the stride calculated from the waveform of the cut out acceleration signal is within the predetermined range based on the stride calculated from the reference-walk-waveform, and the walk cycle calculated from the waveform of the cut out acceleration signal is within the predetermined range based on the walk cycle calculated from the reference-walk-waveform.

Then, in step S27, the shift determining unit 224 outputs to the displaying unit 50 the determination result of whether the attached position of the body motion sensor 102 is shifted from the initially attached position.

The displaying unit 50 displays the determination result, made by the shift determining unit 224, of whether the attached position of the body motion sensor 102 is shifted from the initially attached position. Specifically, if it is determined that the attached position of the body motion sensor 102 is not shifted from the initially attached position, the displaying unit 50 displays a positive mark, for example, "O". If it is determined that the attached position of the body motion sensor 102 is shifted from the initially attached position, the displaying unit 50 displays a negative mark, for example, "X".

The displaying unit 50 may categorize the degree of shift of the attached position of the body motion sensor 102 into a plurality of levels and show the user the target for adjusting the attached position according to the categorized level corresponding to the degree of shift of the attached position of the body motion sensor 102. The degree of the shift of the attached position of the body motion sensor 102 is estimated based on the difference between the maximum peak value calculated from the reference-walk-waveform and the maximum peak value calculated from the waveform of the cut out acceleration signal, the difference between the stride calculated from the reference-walk-waveform and the stride calculated from the waveform of the cut out acceleration signal, or the difference between the walk cycle calculated from the reference-walk-waveform and the walk cycle calculated from the waveform of the cut out acceleration signal.

The displaying unit 50 may display the direction and the distance by which the attached position of the body motion sensor 102 is moved by the user according to the degree of the shift of the body motion sensor 102. The direction and the distance by which the user moves the attached position of the body motion sensor 102 is estimated based on the difference between the maximum peak value calculated from the reference-walk-waveform and the maximum peak value calculated from the waveform of the cut out acceleration signal, the difference between the stride calculated from the reference-walk-waveform and the stride calculated from the waveform of the cut out acceleration signal, or the difference between the walk cycle calculated from the reference-walk-waveform and the walk cycle calculated from the waveform of the cut out acceleration signal.

The shift detecting device 1 of the first embodiment may include a speaker instead of the displaying unit 50. The speaker may output a sound indicating the determination result of Whether the attached position of the body motion sensor 102 is shifted from the initially attached position. If the alarm for the shift of the attached position of the body motion sensor 102 is to be given by a sound, the speaker may output a buzzing sound at a short interval when the shift of the body motion sensor 102 is large or present an indicator by which the user can determine the degree of the shift of the body motion sensor 102 from the initially attached position.

In such a manner, the waveform of the first body motion signal is compared with the reference-walk-waveform while the person walks with the predetermined stride, where the first body motion signal is obtained from the body motion sensor 102 attached to the body of the person to detect the body motion of the person and the reference-walk-waveform is generated from the second body motion signal obtained from the body motion sensor 102 while the person walks with the predetermined stride with the body motion sensor 102 attached to the initially attached position. If the person walks with the predetermined stride with the body motion sensor 102 attached to the same position as the initially attached position, the first body motion signal wave is substantially identical to the reference-walk-waveform. If the person walks with the predetermined stride with the body motion sensor 102 attached to a position shifted from the initially attached position, the first body motion signal wave is not substantially identical to the reference-walk-waveform. It can be determined that the attached position of the body motion sensor 102 is the same as the initially attached position if the first body motion signal wave is similar to the reference-walk-waveform, and it can be determined that the attached position of the body motion sensor 102 is shifted from the initially attached position if the first body motion signal wave is not similar to the reference-walk-waveform. Thus, the shift of the attached position of the body motion sensor 102 from the initially attached position can be detected with high accuracy from the walking motion of the person.

Second Embodiment

A shift detecting system according to a second embodiment will be described based on FIG. 7.

FIG. 7 is a block diagram illustrating a configuration of a shift detecting system according to the second embodiment of the present disclosure. The shift detecting system 2 of the second embodiment includes a first detecting device 3, a second detecting device 4, and a shift detecting device 5. In the second embodiment, the component configured the same as that of the first embodiment is appended with the same reference sign and description thereof is omitted.

The first detecting device 3 includes a foot sole sensor 101 and a communication unit 103. The first detecting device 3 may be provided on a shoe sole or an insole placed inside a shoe. In particular, the foot sole sensor 101 is preferably provided near a heel portion which contacts the foot sole while the person walks. The foot sole sensor 101 detects the change in the gravity center of the walking person and outputs a gravity-center signal. The communication unit 103 transmits the gravity-center signal detected by the foot sole sensor 101 to the shift detecting device 5. The first detecting device 3 and the shift detecting device 5 are connected via a network and can communicate with each other. The network may be, for example, the Internet, a Wireless Local Area Network (LAN), or a Near Field Communication.

The second detecting device 4 includes a body motion sensor 102 and a communication unit 104. The second detecting device 4 is preferably attached to a portion of the trunk of the person near a belt or attached to an ankle or a thigh with a belt wound around the ankle or the thigh. More preferably, the body motion sensor 102 is attached to the waist or a foot so that a cyclic motion of walking can be detected. If the body motion sensor 102 is to be attached to the ankles, the body motion sensor 102 may be attached only to one of the ankles. In the second embodiment, the second detecting device 4 is attached to the front portion of an ankle. The body motion sensor 102 detects the motion of the body of the person and outputs a body motion signal. The body motion sensor 102 is, for example, an acceleration sensor, and the body motion signal is, for example, an acceleration signal. The communication unit 104 transmits the body motion signal detected by the body motion sensor 102 to the shift detecting device 5. The second detecting device 4 and the shift detecting device 5 are connected via a network and can communicate with each other.

The shift detecting system 2 of the second embodiment may not include the first detecting device 3.

The shift detecting device 5 includes a processor 20, a memory 30, a stride presenting unit 40, a displaying unit 50, and a communication unit 60. The processor 20 includes a reference-walk-waveform generating unit 201 and a shift detecting unit 202. The reference-walk-waveform generating unit 201 and the shift detecting unit 202 are configured the same as those of the first embodiment. The memory 30 includes a stride storing unit 301 and a reference-walk-waveform storing unit 302.

The communication unit 60 receives the gravity-center signal transmitted by the first detecting device 3 and outputs the received gravity-center signal to the processor 20. The communication unit 60 receives the body motion signal transmitted by the second detecting device 4 and outputs the received body motion signal to the processor 20.

The operation of the shift detecting system 2 of the second embodiment is the same as the operation of the shift detecting device 1 of the first embodiment except that the shift detecting device 5 receives signals from the first detecting device 3 and the second detecting device 4 via the network.

The reference-walk-waveform generating unit 201, the shift detecting unit 202, the stride storing unit 301, and the reference-walk-waveform storing unit 302 may not be included in the shift detecting device 5 but may be included in a server that is connected to and can communicate with the shift detecting device 5.

The devices according to the present disclosure are described above. The present disclosure is not limited to the embodiments described above. Any idea of an alteration of the above-described embodiment made by a person skilled in the art or of a combination of the components of different embodiments described above may Pall within the scope of one or a plurality of the embodiments of the present disclosure unless such an alteration or a combination departs from the spirit of the present disclosure.

Although each components of the embodiment is a dedicated piece of hardware, the function of the component may be realized by executing a software program suitable for each component. The function of each component may be realized by reading and executing of a software program stored in a storage media, such as a hard disk or a semiconductor memory, by a program executing unit, such as a CPU or a processor.

A part or all of the functions of the device according to the embodiment of the present disclosure typically is realized as a Large Scale Integration (LSI), which is an integrated circuit. These may each be provided as a single chip or a portion or all of them may be included in a single chip. The integrated circuit is not limited to an LSI but may be realized by a dedicated circuit or a general-purpose processor. A Field Programmable Gate Way Array (FPGA), which is an LSI programmable after having been manufactured, or a reconfigurable processor in which a connection or setting of a circuit cell inside the LSI is reconfigurable may be used.

A portion or all of the functions of the device according to the embodiment of the present disclosure may be realized by executing a program by a processor, such as a CPU.

Numbers used above are all exemplarily presented to specifically explain the present disclosure, so that the present disclosure is not limited by the exemplary numbers.

The order of executing the steps shown in the flowchart is an example for specifically explaining the present disclosure. As long as the same effect is obtained, the steps may be executed in an order oilier than the order described above. A portion of the step may be executed at the same time as (in parallel with) another step.

Any modification of the embodiment of the present disclosure made within the scope of an idea made by a person skilled in the art falls within the scope of the present disclosure unless such a modification departs from the spirit of the present disclosure.

The detecting method, the detecting device, and the detecting system according to the present disclosure can detect the shift of the attached position of the body motion sensor from the initially attached position from the walking motion of the person with high accuracy, and can be used as the detecting method, the detecting device, and the detecting system for detecting the shift of the sensor, attached to the body of a person, from the initially attached position.

This application is based on Japanese Patent application No. 2018-095593 filed in Japan Patent Office on May 17, 2018, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A detecting device for determining whether an attached position of a body motion sensor being attached to a body of a person and configured to detect shifting of the body motion sensor from an initially attached position, the device comprising:
   a processor; and
   a memory,
   the processor configured to obtain a reference-walk-waveform by
   detecting a first body motion signal from the body motion sensor while the person walks,
   determining a parameter of a walking condition of the person from the first body motion signal and determining from the parameter a stride of the person walking that generates the first body motion signal from the body motion sensor,
   determining if the determined stride is to be used in detecting a shift of the body motion sensor from the initially attached position, if the determined stride is not to be used in detecting the shift of the body motion sensor from the initially attached position, increasing a first stride presented to the person for obtaining the reference-walk-waveform by a predetermined distance, and determining whether the increased stride presented to the person is to be used in detecting the shift of the body motion sensor from the initially attached position, if the determined stride is to be used in detecting the shift of the body motion sensor from the initially attached position, determining the reference-walk-waveform from the first body motion signal, and saving the determined reference-walk-waveform in the memory, wherein the saved reference-walk-waveform represents a predetermined stride, obtaining a second body motion signal from the body motion sensor while the person walks with the predetermined stride, the body motion sensor being attached to the body of the person and configured to detect the body motion of the person, reading out the obtained reference-walk-waveform from the memory, comparing the read-out reference-walk-waveform with a waveform of the obtained second body motion signal to determine whether an attached position of the body motion sensor is shifted from the initially attached position, and outputting a result of the comparing.

2. A method performed by a computer of determining whether an attached position of a body motion sensor being attached to a body of a person and configured to detect shifting of the body motion sensor from an initially attached position, the method comprising:

obtaining a reference-walk-waveform by detecting a first body motion signal from the body motion sensor while the person walks, determining a parameter of a walking condition of the person from the first body motion signal and determining from the parameter a stride of the person walking that generates the first body motion signal from the body motion sensor, determining if the determined stride is to be used in detecting a shift of the body motion sensor from the initially attached position, if the determined stride is not to be used in detecting the shift of the body motion sensor from the initially attached position, increasing a first stride presented to the person for obtaining the reference-walk-waveform by a predetermined distance, and determining whether the increased stride presented to the person is to be used in detecting the shift of the body motion sensor from the initially attached position, if the determined stride is to be used in detecting the shift of the body motion sensor from the initially attached position, determining the reference-walk-waveform from the first body motion signal, and saving the determined reference-walk-waveform in the memory, wherein the saved reference-walk-waveform represents a predetermined stride, obtaining a second body motion signal from the body motion sensor while the person walks with the predetermined stride;

reading out the obtained reference-walk-waveform from the memory;

comparing the read-out reference-walk-waveform with a waveform of the obtained second body motion signal to determine whether an attached position of the body motion sensor is shifted from the initially attached position; and outputting a result of the comparing.

3. The method according to claim 2, the body motion sensor being configured to detect an acceleration of the body of the person and output an acceleration signal, the method further comprising:

calculating the walking condition including at least one of a maximum value of the acceleration, the stride of the person, and a walk cycle of the person based on the acceleration signal obtained from the body motion sensor, and wherein whether the person is walking with the predetermined stride is determined based on the calculated walking condition.

4. The method according to claim 2, the body motion sensor being configured to detect an acceleration of the body of the person and output an acceleration signal, the method further comprising:

obtaining a gravity-center signal from a pressure sensor that detects a change in a gravity center of the person while the person walks; and calculating the walking condition including at least one of a maximum value of the acceleration, the stride of the person, and a walk cycle of the person based on the acceleration signal obtained from the body motion sensor and the gravity-center signal obtained from the pressure sensor, and wherein whether the person is walking with the predetermined stride is determined based on the calculated walking condition.

5. The method according to claim 3, wherein at least one of a standard deviation of the calculated maximum value of the acceleration, a standard deviation of the stride of the person, and a standard deviation of the walk cycle of the person is calculated, and it is determined that the person is walking with the predetermined stride when at least one of the calculated standard deviation of the maximum value of the acceleration, the standard deviation of the stride, and the standard deviation of the walk cycle is below a threshold value.

6. The method according to claim 2, wherein the reference-walk-waveform is generated by averaging a plurality of body motion signals cut out from the first body motion signal at every walk cycle.

7. The method according to claim 2, wherein the comparing operation determines that the attached position of the body motion sensor is shifted from the initially attached position when at least one of differences, regarding a walk cycle, the stride, and a maximum value, between the reference-walk-waveform and the waveform of the obtained second body motion signal is equal to or higher than a threshold.

8. The method according to claim 2, wherein the body motion sensor is attached to an ankle of the person.

9. A detecting system comprising:
the body motion sensor; and
the detecting device according to claim 1.

* * * * *